United States Patent [19]

Löhn

[11] 4,403,958
[45] Sep. 13, 1983

[54] DENTAL COMPRESSED-AIR MOTOR

[75] Inventor: Gerd Löhn, Biberach, Fed. Rep. of Germany

[73] Assignee: Kaltenbach & Voigt GmbH & Co., Biberach an der Riss, Fed. Rep. of Germany

[21] Appl. No.: 242,051

[22] Filed: Mar. 9, 1981

[30] Foreign Application Priority Data

Mar. 11, 1980 [DE] Fed. Rep. of Germany ....... 3009337

[51] Int. Cl.³ .............................................. A61C 1/02
[52] U.S. Cl. ................................... 433/100; 433/126
[58] Field of Search .................. 433/80, 89, 84, 82, 433/65, 126, 100, 114

[56] References Cited

U.S. PATENT DOCUMENTS 4,217,101  8/1980  Loge ................................. 433/126
4,260,382  4/1981  Thomson ............................ 433/29
4,278,427  7/1981  Lingenhole ....................... 433/100

FOREIGN PATENT DOCUMENTS 608587  5/1959  Italy .................................... 433/100

Primary Examiner—Robert Peshock
Attorney, Agent, or Firm—Scully, Scott, Murphy & Presser

[57] ABSTRACT

A dental compressed-air motor, consisting of a housing in which there is arranged a rotatably supported rotor adapted to be set into rotation by means of operational compressed air which is introduced into the housing through the intermediary of an operational compressed-air inlet conduit, and which includes a rotor shaft connectable with a work tool, wherein the operational compressed-air inlet conduit has associated therewith a regulating device located within the housing, with an externally operable handle for effecting the turning of a rotary slide valve supported within the motor housing for variation of the rotational speed and/or the direction of rotation of the rotor. Furthermore, at one end of the motor housing there are provided coupling means for connection with a dental handpiece supporting the work tool and, at the other end of the motor housing, coupling means in the form of an attachment element for connection with a supply hose conducting compressed air or other media streaming towards or from the motor housing or handpiece, whereby the rotary slide valve is located intermediate the motor and the attachment element and whereby the attachment element is provided with essentially axially incoming and essentially axially further extending media through-passageways which are connected to the media conduits leading to the location of application for the compressed-air motor or the handpiece.

18 Claims, 7 Drawing Figures

DENTAL COMPRESSED-AIR MOTOR

BACKGROUND OF THE INVENTION

1. Field of the Invention

The present invention relates to a dental compressed-air motor, consisting of a housing in which there is arranged a rotatably supported rotor adapted to be set into rotation by means of operational compressed air which is introduced into the housing through the intermediary of an operational compressed-air inlet conduit. The motor includes a rotor shaft connectable with a work tool, wherein the operational compressed-air inlet conduit has associated therewith a regulating device located within the housing, with an externally operable handle for effecting the turning of a rotary slide valve supported within the motor housing for variation of the rotational speed and/or the direction of rotation of the rotor. Furthermore, at one end of the motor housing there are provided coupling means for connection with a dental handpiece supporting the work tool and, at the other end of the motor housing, coupling means in the form of an attachment element for connection with a supply hose conducting compressed air or other media streaming towards or from the motor housing or handpiece. The rotary slide valve is located intermediate the motor and the attachment element and whereby the attachment element is provided with essentially axially incoming and essentially axially further extending media through-passageways which are connected to the media conduits leading to the locations of application for the compressed-air motor of the handpiece.

2. Discussion of the Prior Art

The compressed-air motor, for instance, can be constructed, in accordance with German Laid-open patent application No. 19 41 159, as a turbine with a rotor provided with turbine vanes; pursuant to German Published patent application No. 12 32 789 as a piston motor having a rotor provided with cylinders for pistons, for example, in the form of balls; or pursuant to German Laid-open patent application No. 23 04 666 as a vane motor with a rotor which is provided with slots for radially movable vanes.

A compressed-air motor of the above-mentioned type is the subject matter of earlier German patent application P No. 28 39 632.9. In this compressed-air motor, the attachment element is provided in the same manner as in the compressed-air motor which has become known through the prospectus sheet "KaVo INTRA L-Motor", by being provided in a cap screw-like coupling unit at the end of the supply hose, which can be threaded onto a thread of fixed attachment portion of the motor, whereby the attachment element and the attachment portion are drawn towards each other while producing the media transmission through the intermediary of mutually inserted plug and tube support connections. The required screwing off and screwing on of the coupling nut which is necessary for a separation and a reassembly of motor and attachment element, for example, for the purpose of interchanging differently constructed compressed-air motors, or for the purpose of the oiling or lubricating of the motor effected from the connecting side, for instance, with the aid of a spray nozzle containing a maintenance medium, is always an extremely complex and time-consuming procedure.

Accordingly, it is an object of the present invention to provide in a compressed-air motor of the above mentioned type, an arrangement for the simple and rapid separation and reassembly of the motor and attachment element.

Through German Petty Pat. No. 77 29 110 there has become known a dental compressed-air drive aggregate which, in contrast with the compressed-air motor of the above mentioned type, is not connectable with a dental handpiece supporting the work tool, but is constructed as a compressed-air turbine directly driving the work tool and fixedly built in at one end of the gripping sleeve of a dental handpiece representing a turbine handpiece. At the other end of the gripping sleeve of this known handpiece there is provided an attachment element for the connection of compressed-air or, respectively, other flow media to a supply hose leading towards or from the handpiece. This attachment element of the known handpiece is provided to facilitate a quick coupling, in essence, a simple and rapid separation and reassembly, on the one hand, of the gripping sleeve and the connecting member in addition to the supply hose, and on the other hand, with detachably insertable guide spigot at the inlet apertures of the gripping sleeve which is axially open towards the attachment side, into which there extend the media through-passageways, which presently end with outlet openings extending from the side of the guide spigot, and which are sealed relative to each other while leaving a spacing therebetween, wherein the gripping sleeve includes at the side wall of the inlet apertures, inlet openings associated with the outlet openings of the guide spigot which, for an inserted guide spigot, come into communication with the outlet openings of the latter and from which there extend media conduits leading towards a location of application for the handpiece. Due to the axial spacing and a mutual sealing of the outlet openings of the different media through-passageways, there is obtained a relatively large length for the guide spigot or extension.

The positioning of this relatively lengthy guide spigot within the gripping sleeve of the known handpiece thus presents no difficulties since guide sleeves must in any event have a predetermined length in order to facilitate a secure gripping, primarily in a type of pencil holder, which, without anything else, affords the arrangement of the inlet opening serving for the insertion of the guide spigot. Thereby, also the media conduits which lead to the drive aggregate, for example, cooling media conduits, are not in the way.

Another relationship is obtained when a compressed-air motor built in accordance with the type shown in German patent application P No. 28 39 632.9 should be provided with an attachment element with a lengthy guide spigot as is known from German Petty Pat. No. 77 29 110. In this compressed-air motor, at the hose end, for positioning the lengthy guide spigot of the attachement element, due to the rotary slide valve of the regulating device being in the way, either the entire regulating device must be omitted, or a special extension sleeve must be provided whereby for a coupled on handpiece there was obtained such a large overall length and such a high total weight, that the handpiece inclusive the compressed-air motor and attachment element would become unwiedly. The omission of the regulating device would eliminate the advantage of the capability of varying the rotatinal speed or the direction of rotation.

SUMMARY OF THE INVENTION

The present invention thus attains the object of providing a compressed-air motor of the above mentioned type which, while retaining the advantage of the regulating capability over the rotational speed or direction of rotation is adapted to be provided with an attachment element having a relatively long guide spigot, which is known for turbine handles, to facilitate a quick coupling, without that hereby the overall length or the total weight of the compressed-air motor inclusive of handpiece and attachment element becomes disturbingly greater than in the application of the known compressed-air motor which is connected to the attachment element through the intermediary of a coupling nut.

The advantages which are achieved through the present invention can be essentially ascertained in that, as a result of the inserting aperture of the rotary slide valve serving for receiving of the guide spigot, while retaining the rotational speed or direction of rotation regulating capability, there is obtained a compact construction with only an overall length of the handpiece besides the compressed-air motor and attachment element, which is not larger than that of the known compressed-air motor. Concurrently, the proposed construction provides for a problemless conveyance of the media conduits which lead to the work tool, for example, for cooling media such as water, air, spray or the like, through the motor housing. Moreover, the attachment element in addition to the guide spigot can coincide with the construction pursuant to German Petty Pat. No. 77 29 110 and, correspondingly, conformed with the inlet opening of the motor and the insertion aperture of the rotary slide valve so that one and the same attachment element can be rapidly and simply connected to not only differently designed or constructed compressed-air motors, but even to turbine handpieces constructed in accordance with the above-mentioned German Petty patent.

BRIEF DESCRIPTION OF THE DRAWINGS

Reference may now be had to the following detailed description of preferred embodiments of the invention, taken in conjunction with the accompanying drawings; in which.

DETAILED DESCRIPTION

Figure 1:
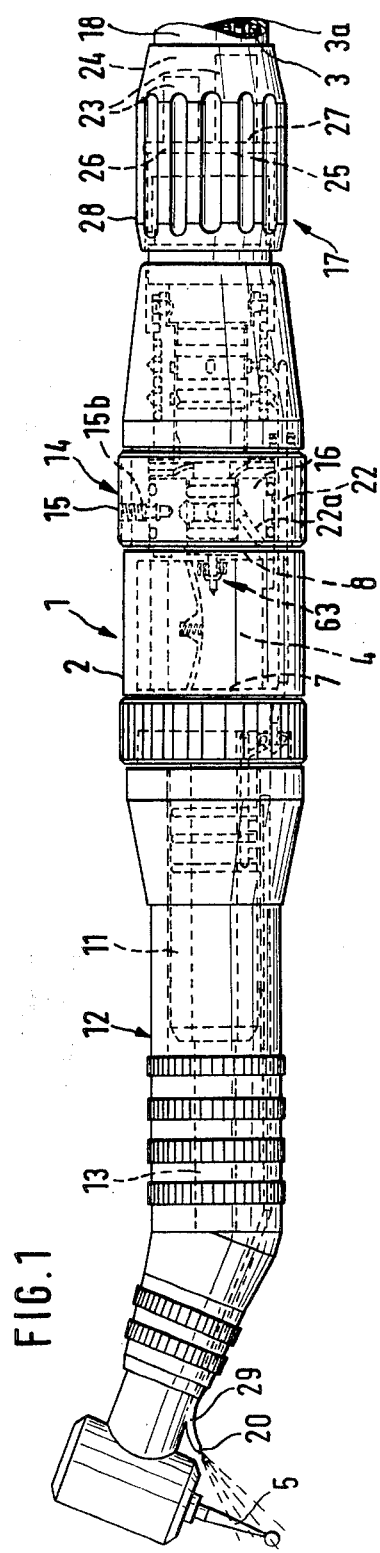
FIG. 1 is a side view of a dental compressed-air motor with a handpiece coupled thereto, and a coupled attachment element.

Dental compressed-air motor 1, which is constructed as a vane motor, consists of a housing 2 forming the stator with an interiorly located rotor sleeve 2a, in which there is arranged a rotatably supported rotor 4 adapted to be placed into rotation through compressed drive air which is introduced into the housing through the intermediary of an operative compressed-air inlet conduit 3, and which rotor includes a rotor shaft 6 connectable with a work tool 5, for example, a drill. The rotor 4 is arranged within the housing 1 intermediate the faces of cover-like end surfaces 7, 8 and supported by means of ball bearings 8a. Vanes 10 are radially movably supported within longitudinal slots 9 in the rotor 4. The rotational speed of the vane motor can, for example, consist of about 20,000 to 100,000 revolutions per minute.

At its end towards the work tool, the motor 1 possesses coupling means in the form of an extension 11 for the insertion into a receiving apertures of a dental handpiece 12 mounting the work tool 5 and being constructed as an attachment member. The handpiece 12 is detachably connectable with the compressed-air motor in a known and therefore not illustrated manner. During the formulation of this connection, a drive shaft 13 located interiorly of the handpiece 12 comes also into engagement with the rotor shaft 6 of the motor 1. The drive shaft 13 places the work tool 5 into rotation through a plurality of gears (not shown) or the like arranged at various angles.

Figure 7:
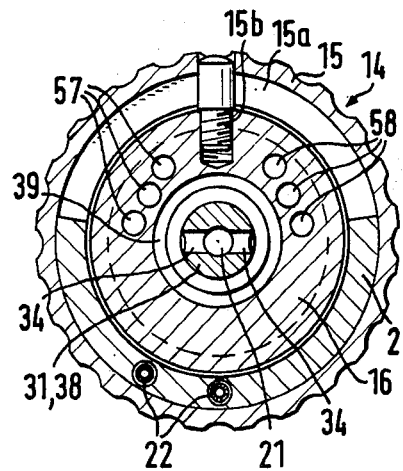
FIG. 7 is a sectional view taken along line VII—VII in FIG. 3.

The operational compressed-air inlet conduit 3 is associated with a regulating device 14 located within the housing 2 with a handgrip 15 adapted to the operated from the exterior and constructed as a rotary ring for the turning of a rotary slide valve 16 which supported within the motor housing 2 for varying the rotational speed and/or the direction of rotation of the rotor 4. The handle 15 is connected by means of a follower screw 15b, which projects through a radial guide slot 15a in the housing 2 (see FIG. 7), with the rotary slide valve 16. The rotary slide valve 16 is sealed by means of O-rings 66 located in annular grooves with regard to the wall of the housing 2.

Provided at the end of the motor housing 2 remote from the handpiece are coupling means in the form of a receiving aperture 30 and an attachment element 17 (elucidated in detail hereinbelow) for connection with a flexible supply hose 18 conveying flowing media in special conduits 3, 3a, for example, compressed drive air, exhaust air, compressed cooling air, cooling water or the like, towards or from the motor housing 2 or handpiece 12.

Figure 3:
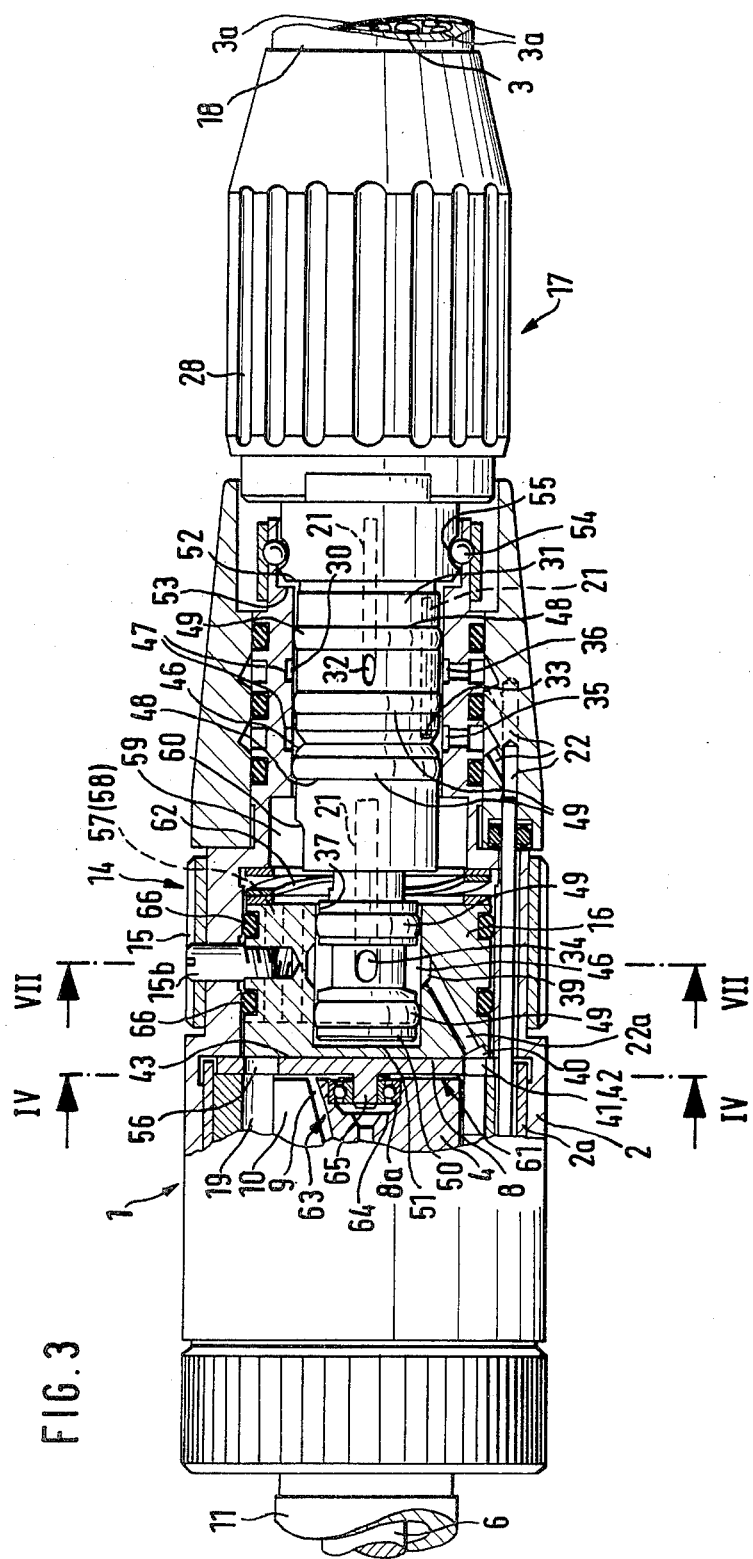
FIG. 3 is an enlarged side view, partly in section, of the compressed-air motor with the attachment element shown coupled thereto.

As illustrated in FIGS. 1 and 3, the rotary slide valve 16 of the regulating device 14 is located intermediate the rotor 4 and the attachment element 17 is provided with essentially axially incoming and essentially axially further extending media through-passageways 21, which are connected with the media conduits 22, 22a leading to the locations of utilization 19, 20 of the compressed-air motor 1 or the handpiece 12. As its other end, the only partially illustrated media through-passageways 21 are connected through the inlet connectors 23 in FIG. 1, which are inserted into the respective inserting apertures of an attachment portion 24 of the supply hose 18, with the flexible conduits 3, 3a located within the last-mentioned hose. The end face of the attachment element 17 towards the hose end is designated, pursuant to FIG. 1, with reference numeral 25 and the end face of the hose connector portion 24, lying thereagainst with the interposition of the seal 26, is designated with reference numeral 27. The hose connector portion 24 possesses a screw cap-like coupling nut 28 which is threaded onto an outer thread (not shown) of the attachment element 17. By means of the coupling nut 28, the end faces 25 and 27 are sealingly drawn against each other. With respect to the location of media utilization 19, this relates to the displacement space of the compressed-air motor 1 which is acted upon by the media conduit 22a, and with the respect to the media use location 20 to the outlet of a cooling medium tube 29 which is connected with the two lower media conduits 22 shown in FIG. 3.

The attachment element 17 is provided with an axial guide spigot or extension 31 detachably insertable into an elongate receiving aperture 30 of the motor housing 2 open towards the connecting side, in which there extend the media through-passageways 21, which presently end in outlet openings 32, 33, 34 from the side of the guide spigot 31, which are arranged so as to be sealed relative to each other and to leave a relative axial spacing therebetween.

The motor housing 2, at the sidewall of the receiving aperture 30 possesses inlet openings 35, 36 associated with the cooling medium outlet apertures 32, 33 of the guide spigot 31 which, at an inserted guide spigot are in communication with the outlet apertures 32, 33 of the last-mentioned, and from which there extends the media conduits 22, 29 leading to the location of utilization 20 of the handpiece 12.

As may be best ascertained from FIG. 3, the rotary slide valve 16 is provided with a central cylindrical inserting aperture 37 for the receipt of the similarly cylindrical free end region 38 (FIG. 2) of the guide spigot 31. The above-mentioned end region 38 evidences two side outlet apertures 34 conveying compressed drive air (refer also to FIG. 7), which in each rotational position of the rotary slide valve are in communication with one or more of the compressed drive air inlet apertures 39 at the side wall of the inserting aperture 37, from which there extend media conduits 22a representing a plurality of compressed drive air passageways within the rotary slide valve 16, whose outlet apertures 40 can be brought into superposition with an essentially elongate arcuately extending inlet opening 41 arranged in the end surface 8 of the motor housing 2 of a conduit or conduits 42 in the motor housing 2 and leading to the displacement space of the rotor 4 representing a location of utilization 19.

Figure 4:
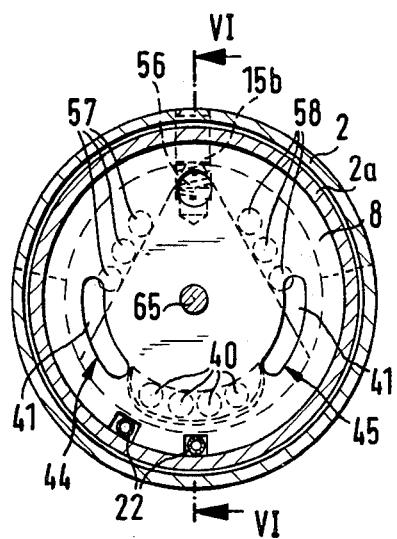
FIG. 4 is a sectional view taken along line IV—IV in FIG. 3.
Figure 5:
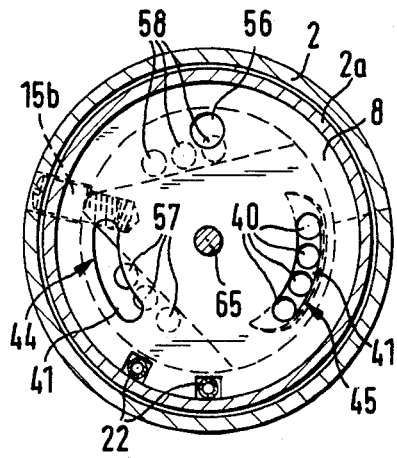
FIG. 5 is a representation similar to FIG. 4 at changed rotary slide valve position.
Figure 6:
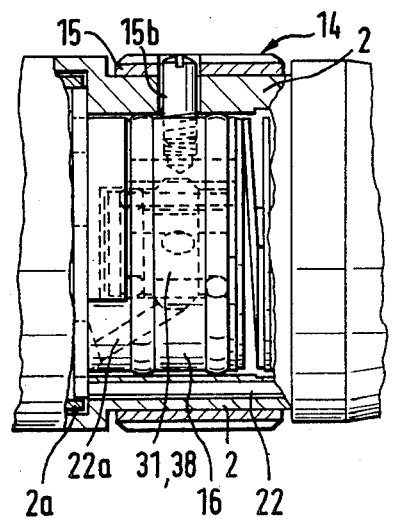
FIG. 6 is a sectional view taken along line VI—VI in FIG. 4.

The outlet apertures 40 of the compressed drive air passageways 22 in the slide valve located in the rotor-sided end surface of the rotary slide valve 16, as shown in a comparison of FIGS. 4 and 5, in accordance with the rotational postion of the rotary slide valve 16, are movable, for varying the compressed air infeed per unit of time, in effect, for varying the rotational speed of the rotor, so as to be brought into superposition with a larger or smaller cross-section of the inlet openings 41. The rotated position of the rotary slide 16 as shown in FIG. 4 signifies th standstill of the rotor 4 and the rotated position shown in FIG. 5 illustrates rotation towards the right.

From FIGS. 4 and 5 there may be further ascertained that two inlet openings arrangements 44 and 45 are located on essentially a circular arc, and that the outlet openings 40 of the rotary slide valve 16, pursuant to the rotational position of the latter for varying the rotational direction of the rotor can be brought into superposition with one of the two inlet opening arrangements 44, 45, wherein both inlet opening arrangements 44, 45 are arranged at a predetermined radial distance to the rotor-sided end surface 43 of the rotary slide valve of the parallel and sealingly contacted end surface 8 of the motor housing 2 in the one superimposed position at right-hand running of the rotor, and at running towards the left in the other covering position, whereby of the two inlet opening arrangements 44, 45, pursuant to the selected superimposed position, one serves alternatingly for the further conduction of the compressed drive air and the other for the reconveyance of the exhaust air exiting from the displacement space.

Figure 2:
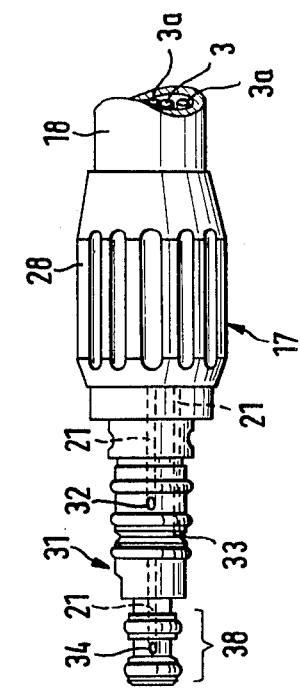
FIG. 2 illustrates the attachment element alone in a side view.

The outlet apertures 32, 33, 34 of the media through-passageways 21 can open radially from the circumference of the guide spigot 31. The outlet opening 33 which, for example, conveys cooling water, and the compressed drive air conveying opening 34 of the media through-passageways 21, particularly as shown in FIGS. 2 and 3, open from a side or bottom wall of generally V or U-shaped annular pasageways 46 as viewed in the longitudinal sectional plane of the guide spigot 31. Similarly, annular passageways 47 can be provided in the side wall of the receiving aperture 30.

The entire guide spigot 31 is circularly shaped in cross-section, however, it possesses in sections extending from its end region 38, an increasing diameter, referring, for example, to FIG. 2. Hereby, the receiving aperture 30 provided in the motor housing 2 possesses a cross-section in conformance with the cross-section of the guide spigot.

The outlet openings 32, 33, 34 of the media through-passageways 21 which are distributed over the axial length of the guide spigot 31 are presently arranged between two sealing elements 49 of the guide spigot 31 which are positioned so as to come into contact with the side walls of the receiving aperture 30, and which are formed as O-rings arranged in annular grooves 48. The annular sealing elements 49 consist of a material with a smooth surface so that when the dentist rotates the compressed-air motor relative to the attachment element 17, they will serve as rotary bearings.

Effected especially rapidly simply, in essence through axial pull or pressure, is the separation or reassembly of the compressed-air motor 1 and the attachment element 17, in that the attachment element 17 and the motor housing 2 are provided with locking or contact means 50 to 55 limiting the inserting movement of the guide spigot 31 at an automatic assumption of a self-releasing latching position. Such stop or contact media can be formed by the end surface 50 of the guide spigot 31 with the bottom 51 of insert aperture 37, or the annular shoulder 52 of the guide spigot 31 with an annular projection 53 on the receiving aperture 30. Furthermore, the latching means can be formed by locking balls 54 resiliently supported in the side wall of the receiving aperture 30 and through an annular groove 55 on the guide spigot 31 provided for engagement with the balls.

In particular there can be ascertained from FIGS. 3 through 5 that for the exhaust air exiting from the displacement space 19 of the compressed-air motor 1, there is provided in the end face 8 of the motor 1 parallel to the rotor-sided end surface 43 of the rotary slide valve 16 at least one exhaust outlet opening 56 which in each of the two superimposed positions for right running or left running is adapted to be brought into superposition with one of two through-passageway groups 57, 58 of the rotary slide valve 16. The through-passageway groups 57, 58 open into an annular chamber 59 provided in the side wall of the receiving aperture 30, from which the exhaust air flows to freedom through an inlet opening 60 into a return passageway (not shown) of the guide spigot 31 through the attachment element 17.

As shown particularly in FIG. 3, the end surface 8 of the motor 1 which is parallel to the rotor-sided end surface 43 of the rotary slide valve 16 is formed by a distributor disk 61 which is fixed to the housing. Furthermore, FIG. 3 shows that the rotary slide valve 16 is maintained, under the effect of a retaining spring 62, with its rotor-sided end surface 43 sealed against the end surface 8 of the motor which is parallel to this end surface 43. Hereby, the mutually contacting surfaces 43, 8 evidence a flat polished surface.

From FIG. 3 there may be further ascertained that the end surface 8 of the motor 1 which extends in parallel to the rotor-sided end surface 43 of the rotary slide valve 16 is provided with a bearing support 63 having a ball bearing 8a for the rotor 4. Hereby the bearing support 63 consists of a bearing spigot 65 which is in engagement with an axial recess in the rotor 4' and which is arranged at the rotor-side on the end surface 8, whereby the ball bearing 8a is located between the bearing trunnion 65 and the side wall of the axial recess.

In a manner not illustrated herein, the bearing can also consist of a bearing cutout provided in the end surface 8 for receiving a shaft end of the rotor 4, whereby the rotary slide valve 16 can also possess at its rotor sided end surface 43 a recess for receiving the extended shaft end of the rotor 4. Hereby, the recess of the rotary slide valve 16 can be provided as a cutout for the movement through of the elongated shaft end in the bottom of the inlet aperture 37 of the rotary slide valve which is provided for the guide spigot and the end surface 50 of the guide spigot 31 is itself provided with a recess for receiving of the shaft end.

Moreover, in a manner not shown, the bearing can consist of a bearing trunnion arranged at the rotor-sided end surface 43 of the rotary slide valve 16 and projecting through a cutout provided in the end surface 8, and which stands in engagement with an axial recess in the rotor.

What is claimed is:

1. In a dental compressed-air motor, a housing; a rotatably supported rotor in said housing adapted to be rotated by compressed drive air introduced through a compressed drive air inlet conduit; a rotor shaft connectable with a work tool on said rotor, regulating means including externally operable handgrip means in said housing and being turnable through said regulating means for varying the rotational speed and/or the direction of rotation of said rotor; first coupling means at one end of said housing for connection with a dental handpiece mounting said work tool and second coupling means formed by an attachment element for connection with a supply hose conveying compressed air or other flow media towards or from said housing and said handpiece, said rotary slide valve being arranged intermediate said rotor and said attachment element, said attachment element including essentially axially entering and axially extending media through-passageways connected with media conduits leading to the location of use of the compressed-air motor and handpiece; the improvement comprising:

said attachment element including an axial guide spigot axially detachably insertable into a receiving aperature of said housing open towards the connecting side and into which there extends said media passageways and terminate in outlet openings at the side of said guide spigot, said outlet openings being sealed relative to each other and being at predetermined spacings, said housing including inlet openings on the side wall of the receiving aperture associated with the outlet openings of the guide spigot which are in communication with the outlet openings of said guide spigot upon insertion of the latter and from which there extend the media conduits leading to a location of use for said handpiece; said rotary slide valve including a central cylindrical insertion aperture extending substantially along the entire axial length of the rotary slide valve for receiving a cylindrical end portion of said guide spigot, said end portion having at least one side outlet opening for compressed drive air which in each turned position of the rotary slide valve is in communication with at least one compressed drive air inlet opening on the side wall of the insertion aperture and from which there extends at least one media conduit representing the compressed drive air passageways in said rotary slide valve, and whose outlet openings are adapted to be superimposed on at least one inlet opening of at least one conduit leading to the displacement space of said rotor in said housing representing a location of use.

2. Dental compressed-air motor as claimed in claim 1 said compressed drive air passageways extending to the rotor-sided end face of the rotary slide valve and exiting therefrom, said outlet openings of the passageways being superimposable with larger or smaller cross-section on the inlet openings of the conduits leading to the displacement space of the rotor according to the turned position of the rotary slide valve for varying the rotor speed, the outlet openings being superimposable with one of at least two inlet openings of the conduits leading to the displacement space according to the turned position of the rotary slide valve for changing the rotational direction of the rotor, both inlet opening arrangements being in an end face of the housing in parallel and sealed relationship to the rotor-sided end face of the rotary slide valve and at a predetermined spacing so as to be in one superimposed position at the right-hand running of the rotor and in the other superimposed position at the left-hand running whereby of the two arrangements according to selected superimposed postion one alternatingly serves for the further conveyance of the compressed drive air and the other for the reconveyance of exhaust air emanating from the displacement space.

3. Dental compressed-air motor as claimed in claim 1 or 2, wherein the outlet openings of the media passages open radially from the circumference of said guide spigot.

4. Dental compressed-air motor as claimed in claim 1 or 2, said outlet openings of the media passageways opening from the side wall and bottom wall of generally U-shaped or V-shaped annular passageways in the longitudinal section of said guide spigot.

5. Dental compressed-air motor as claimed in claim 1, said guide spigot being circular in cross-section, said receiving aperture in said housing having a cross-section conformed to the cross-section of said guide spigot.

6. Dental compressed-air motor as claimed in claim 1, wherein the outlet openings of said media passageways are distributed over the length of said guide spigot.

7. Dental compressed-air motor as claimed in claim 1, said outlet openings of the media passageways being arranged intermediate two sealing elements contacting the side wall of said receiving aperture.

8. Dental compressed-air motor as claimed in claim 1, said attachement element and said housing including latching and contact means for limiting the inserting movement of said guide spigot at the automatic assumption of a self-releasing latched position.

9. Dental compressed-air motor as claimed in claim 1, said end surface of the motor facing towards the rotor-sided face of the rotary slide valve having at least one exhaust air outlet opening for the exhaust air from said motor displacement space, said outlet openings being superimposable upon one of two passageway grooves of the rotary slide valve in both right-hand and left-hand effecting covering positions.

10. Dental compressed-air motor as claimed in claim 1, said motor end surface facing the rotary slide valve comprising a distributor disc fastened to said housing.

11. Dental compressed-air motor as claimed in claim 1, comprising a retaining spring for sealingly maintaining said rotary slide end surface against the end surface of said motor.

12. Dental compressed-air as claimed in claim 11, said facing surfaces having a flat polished finish.

13. Dental compressed-air motor as claimed in claim 1, said motor end surface facing the rotary slide valve having bearing means for said rotor.

14. Dental compressed-air motor as claimed in claim 13, said bearing means comprising a bearing trunnion in engagement with said rotor.

15. Dental compressed-air motor as claimed in claim 13, said bearing means comprising a cutout in said end surface for receiving a shaft end of said rotor.

16. Dental compressed-air motor as claimed in claim 15, said rotary slide valve end surface having a recess for receiving the extended shaft end of said rotor.

17. Dental compressed-air motor as claimed in claim 16, said recess in said rotary slide valve being a cutout in the bottom of the valve for the insertion aperture of the guide spigot, the end face of said guide spigot including a recess for receiving the shaft end.

18. Dental compressed-air motor as claimed in claim 13, said bearing means having a bearing trunnion on the rotor-sided end face of the rotary slide valve extending through said cutout, said trunnion being in engagement with said rotor.

* * * * *